United States Patent [19]
Stewart

[11] Patent Number: 6,030,378
[45] Date of Patent: Feb. 29, 2000

[54] METHOD OF HAIR REMOVAL BY TRANSCUTANEOUS APPLICATION OF LASER LIGHT

[76] Inventor: Bob W. Stewart, 5745 Pandora Ave., Cincinnati, Ohio 45213

[21] Appl. No.: 09/084,294

[22] Filed: May 26, 1998

[51] Int. Cl.[7] .................................................. A61N 5/06
[52] U.S. Cl. ....................................... 606/9; 606/2
[58] Field of Search ................... 606/9, 10, 11, 606/12, 2, 15, 16, 17

[56] References Cited

U.S. PATENT DOCUMENTS

| | | | |
|---|---|---|---|
| 4,388,924 | 6/1983 | Weissman et al. | 606/9 |
| 5,464,436 | 11/1995 | Smith | 606/9 |
| 5,595,568 | 1/1997 | Anderson et al. | 606/9 |
| 5,647,866 | 7/1997 | Zaias et al. | 606/9 |
| 5,817,089 | 10/1998 | Tankovich et al. | 606/9 |

*Primary Examiner*—Lee Cohen
*Assistant Examiner*—Sonya Harris

[57] ABSTRACT

A method of hair removal, used primarily for cosmetic purposes, comprising the transcutaneous use of laser light having a wavelength which targets the sebum found in the follicle and coating the hair, heating the sebum which transfer heat first to the hair and hair root and then to the papilla and papillary blood vessels via conduction, thus destroying the hair by photothermolysis while avoiding significant damage to surrounding skin or tissue.

4 Claims, 2 Drawing Sheets

METHOD OF HAIR REMOVAL BY TRANSCUTANEOUS APPLICATION OF LASER LIGHT

BACKGROUND OF THE INVENTION

1. Field of the Invention

The invention relates generally to a method of permanent hair removal using laser light. More specifically, the invention relates to the transcutaneous use of laser light to target the sebum that coats the hair, heating the sebum which transfers heat first to the hair and hair root and then to the papilla and papillary blood vessels via conduction, thus destroying the hair by photothermolysis while avoiding significant damage to surrounding skin or tissue.

2. Description of the Prior Art

Currently available laser hair removal methods may be classified as either intrafollicular or transcutaneous in nature. Intrafollicular methods comprise the delivery of laser light through a small probe tip which is inserted into the hair follicle. The light utilized is of a wavelength which is readily absorbed by either the melanin in the hair or the hemoglobin in the blood vessels surrounding the papilla. This absorption of light energy produces heat, resulting in damage to the hair shaft, photocoagulation of the tissue surrounding the papilla, and subsequent destruction of the hair. This process is a painstaking, time-consuming process which must be administered by a skilled operator. When targeting melanin, this method losses effectiveness when used on lighter haired patients.

Some transcutaneous laser hair removal methods currently available utilize a substance which is massaged into the skin to penetrate the hair ducts. After cleaning the substance from the skin's surface, light of a wavelength which passes through the skin, but which is absorbed by the substance, is directed onto the treated area. The absorption of energy by the substance applied to the hair duct causes photocoagulation of the tissue surrounding the papilla and results in destruction of the hair. Although this method allows for treatment of a sizable area of skin, it requires the inconvenient, time consuming application of the light-absorbing substance. In addition, great care must be taken to completely remove the substance from the skin's surface prior to the laser treatment to avoid damage to the skin.

Other transcutaneous laser hair removal methods involve the delivery of light which is absorbed to one extent or another by the melanin in the base of the follicle. Wavelengths utilized range from the deep red to the very near IR (<900 nm). This light is only weakly absorbed by blood and blood components, enabling it to pass relatively unabsorbed through light-colored skin. Dark-skinned individuals and persons with lighter-colored hair are not good candidates for hair removal in this approach.

Because of the disadvantages associated with both methods of hair removal in use today, a new method is needed which provides faster, more convenient, and less painful permanent hair removal without damage to the patient's skin.

SUMMARY OF THE INVENTION

The invention relates to a method of permanent hair removal used primarily for cosmetic purposes. This method comprises the transcutaneous use of laser light having wavelengths in either the 900–940 or the 1200–1300 nanometer ranges wherein the light is directed onto an area of skin on which hair removal is desired. Light in these wavelength bands passes through the skin with only minimal absorption by blood, blood components, and melanin. These wavelengths are, however, readily absorbed by the lipid components of sebum, a substance found in every follicle and one which coats every hair. Absorption of the light energy by the sebum produces heat, which damages, via conduction, the hair shaft and root and also can photocoagulate the blood vessels and tissue surrounding the papilla, resulting in destruction of the hair and preventing its re-growth.

There are numerous problems associated with the hair removal methods in the field of prior art. Some of these methods are painful for the patient. Others have varying effectiveness depending on the skin and hair color of the patient. Most must be administered by highly skilled operators to reduce the risk to the patient. All of these methods involve expensive, painstaking, and time-consuming processes. In addition, all carry substantial risk of skin damage if not performed properly.

It is an object of the invention to provide a hair removal method which: 1) is fast and convenient; 2) is less painful; 3) is effective on hair of all types; 4) has reduced risk for skin damage; and 5) utilizes a low cost, low maintenance, and low power consumption laser source. Further objects and advantages of the invention will become apparent from a consideration of the drawings and description.

Figure 1:
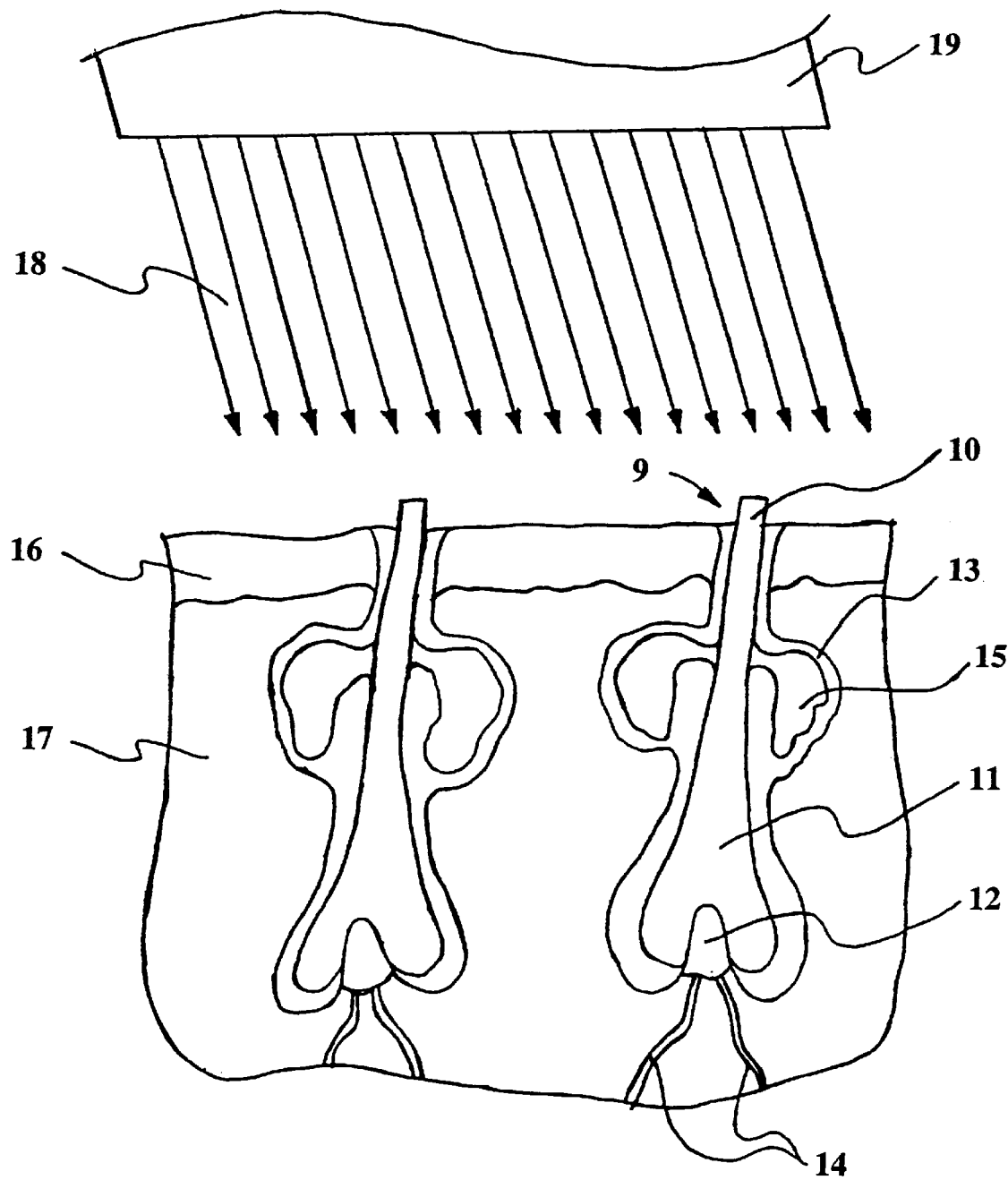
FIG. 1 is a sectional view of an area of skin showing the structure of hair and skin and the transcutaneous application of laser light.

WING REFERENCE NUMERALS hair
shaft
root
papilla
follicle
blood vessels
sebaceous glands
epidermis
dermis
laser light
fiber optic probe tip

DESCRIPTION OF THE PREFERRED EMBODIMENT

Description:

FIG. 1 illustrates the preferred embodiment of the invention. As shown, laser light 18 emanates from the probe tip 19 of a fiber optic cable, not shown, and is directed onto the surface of the skin. The other end of the fiber optic cable is connected to a laser light source, also not shown. The size and shape of the light beam may be customized to meet the requirements of any individual application. FIG. 1 also illustrates the structure of hairs 9 and the surrounding upper and lower skin layers, known as the epidermis 16 and the dermis 17, respectively. Hair 9 comprises shaft 10, shown clipped near the surface of the skin, and root 11. Follicle 13 is a sac which encloses shaft 10, root 11, and adjacent sebaceous glands 15. The sebaceous glands produce a lipidbased substance, sebum, which coats the hair and skin. Located at the lower end of follicle 13 is the papilla 12, which is fed by blood vessels 14 and provides nourishment to root 11. In order to prevent regrowth of hair 9, it is the papilla 12 and, possibly, the papillary blood vessels 14 which must be damaged sufficiently to prevent continued nourishment of root 11.

Figure 2:
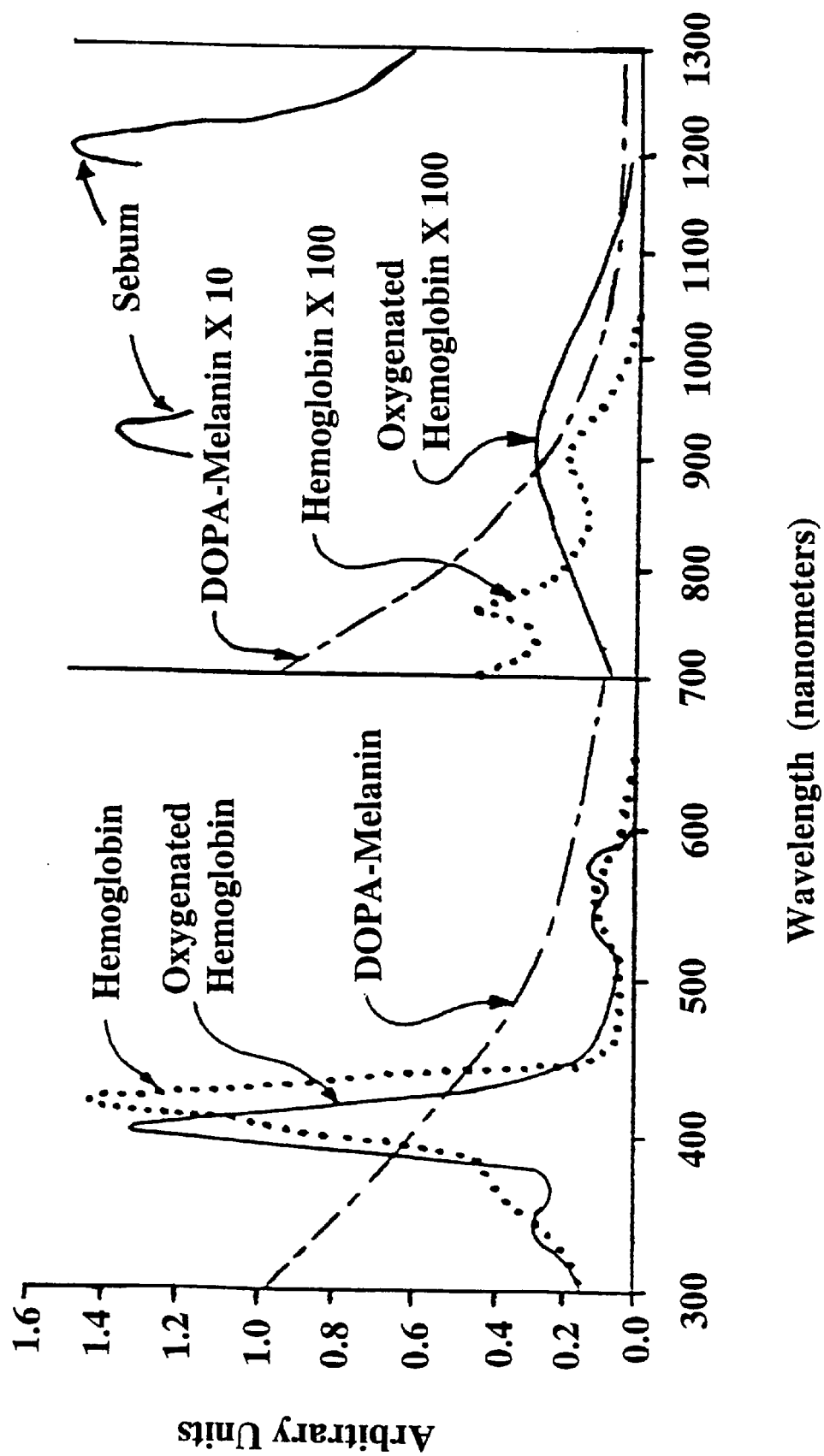
FIG. 2 is a graph showing the absorption spectrum of hemoglobin, oxy-hemoglobin, and melanin in the visible and near infrared light ranges, as well as a portion of the absorption spectrum of sebum in the 900–940 nm and the 1180–1300 nm ranges.

FIG. 2 illustrates the high absorption of light in the 900–940 nm and the 1200–1300 nm wavelength ranges by sebum relative to the absorption by the major tissue chromophores melanin, hemoglobin, and oxyhemoglobin. These absorption characteristics of sebum, hemoglobin, oxyhemoglobin, and melanin allow the transcutaneous use of light of the chosen wavelength to target the sebum in the hair follicle and coating the hair itself and to subsequently destroy the papilla without damage to the surrounding tissue.

The preferred embodiment of the invention primarily utilizes laser light 18 having wavelength in either the 900–940 nanometer or the 1200–1300 nm ranges. As indicated in FIG. 2, light of this wavelength passes through the dermis 17 and the epidermis 16 with only minimal absorption by blood, blood components, and melanin. These wavelengths are, therefore, readily and primarily absorbed by sebum, which is found in the follicles of hair of all colors. In fact, hair is known to be highly adsorbent of oils of many types, sebum being one, being a complex mixture of triglycerides, fatty acids, wax esters, squalene, and cholesterol. These two facts result in the sebum-coated hair being an effective target for light in the specified ranges. Absorption of the light energy by the sebum produces heat, which, being conducted to the hair, damages the hair shaft 10 and root 11. This heat may also photocoagulate the blood vessels 14 feeding the papilla 12, resulting in destruction of the hair 9 and increasing the probability of permanent removal.

High absorption by sebum and low absorption by melanin, blood, and blood components are not the only considerations in the choice of wavelength. Water is a major component of tissue as well. Water absorption of light in the 900–940 nm range is negligible. The penetration depth of light in the 1200–1300 nm range is around 1 cm. Either of these two wavelength bands can be successfully and safely used for hair removal. Sebum also has a strong absorption band in the 1600–1700 nm range. Water absorption of light in this range is probably too high to allow successful and safe use of this light for hair removal purposes.

In the preferred approach, the surface of the skin is cleaned with an sebum-removing substance such as isopropyl alcohol. Next, the hair is closely trimmed, but not shaven. After the area is lased, a "lint roller" can be used to painlessly remove the hair from the follicles. Sebum which is present on the portion of the hair outside the follicle and on the surface of the skin will be removed prior to lasing in this procedure. Therefore, no damage to the skin will result.

Power level and duration of the laser pulse directed onto the skin must be carefully chosen to optimize the conduction of heat from the hair shaft and root to the papilla. As an example, a 0.1 second pulse from a laser delivering a power level of approximately 25 milliwatts per hair to the root would deliver sufficient energy to the hair shaft and root to result in significant damage to the papilla and a high probability of permanent hair removal. Use of a shorter, higher energy laser pulse will rapidly vaporize the hair, resulting in hair removal below the surface with little probability of permanent hair destruction. Pulses of less than 0.0001 seconds in duration having sufficient energy to damage hair can lead to very explosive, i.e. photoacoustic, absorption and to hyper- or hypo-pigmentation. Conversely, a pulse longer than 0.5 seconds can result in damage to the surrounding tissue and possible scarring.

Although the above description contains specificities pertaining to laser light wavelength, pulse duration, and power level, these specificities should not be construed as limitations on the scope of the invention, but rather as an exemplification of one preferred embodiment thereof. Variations in laser wavelength, pulse duration, and power level may be possible without significantly reducing the effectiveness of the method. The invention contemplates all variations in these, and all other laser parameters, which accomplish an equivalent result.

We claim:

1. A method for permanently removing hair from skin by means of laser light having a wavelength which passes through the skin with minimal absorption and which is substantially absorbed by the sebum component of the hair follicle and substantially not absorbed by the melanin component of the hair itself, wherein said laser light is directed onto the surface of said skin using an apparatus with optical elements which are not in contact with said skin and for a period of time sufficient to cause heating of said sebum, resulting in the transfer of heat to the hair itself by conduction and the destruction of said hair.

2. The method of claim 1, wherein said wavelength of said laser light is 900–940 nanometers.

3. The method of claim 1, wherein said wavelength of said laser light is 1200–1300 nanometers.

4. The method of claim 1, wherein the a pulse of said laser light is 1 seconds to 0.5 seconds in duration, the duration chosen to optimize the heat conduction to the papilla of said hair.

* * * * *